(12) United States Patent
Lowery et al.

(10) Patent No.: US 8,190,229 B2
(45) Date of Patent: May 29, 2012

(54) SENSOR HOLDER

(75) Inventors: Guy Russell Lowery, San Juan Capistrano, CA (US); Al Schiff, Richland, MI (US); Robert J. Kopotic, Jamul, CA (US)

(73) Assignee: ConMed Corporation, Utica, NY (US)

( * ) Notice: Subject to any disclaimer, the term of this patent is extended or adjusted under 35 U.S.C. 154(b) by 1464 days.

(21) Appl. No.: 11/536,244

(22) Filed: Sep. 28, 2006

(65) Prior Publication Data

US 2007/0142717 A1 Jun. 21, 2007

Related U.S. Application Data

(60) Provisional application No. 60/721,823, filed on Sep. 29, 2005.

(51) Int. Cl.
*A61B 5/1455* (2006.01)

(52) U.S. Cl. ........................................ 600/344; 600/323

(58) Field of Classification Search ................... 600/323, 600/344; 73/866.5
See application file for complete search history.

(56) References Cited

U.S. PATENT DOCUMENTS

| 5,644,093 | A  | * | 7/1997  | Wright et al. ............... 73/866.5 |
| 5,758,644 | A  |   | 6/1998  | Diab et al. |
| 6,839,585 | B2 |   | 1/2005  | Lowery et al. |
| 2003/0166998 | A1 | * | 9/2003  | Lowery et al. ............... 600/323 |
| 2003/0181799 | A1 | * | 9/2003  | Lindekugel et al. .......... 600/344 |
| 2005/0090725 | A1 | * | 4/2005  | Page et al. ..................... 600/344 |
| 2006/0258939 | A1 | * | 11/2006 | Pesach et al. ................ 600/438 |

* cited by examiner

*Primary Examiner* — Eric Winakur
*Assistant Examiner* — Chu Chuan (JJ) Liu

(57) ABSTRACT

The present invention is directed to holders for a sensor. The holders apply pressure to the sensor to prevent a venous blood signal without dampening the arterial blood signal and are optically opaque to shield ambient light from reaching the sensor.

10 Claims, 7 Drawing Sheets

SENSOR HOLDER

RELATED APPLICATIONS

This application claims priority to U.S. Provisional Application No. 60/721,823, filed Sep. 29, 2005, which is incorporated by reference herein.

BACKGROUND OF THE INVENTION

Noninvasive reflectance pulse oximetry has recently become an important new clinical technique with potential benefits in fetal and neonatal monitoring. The main reason for this application is the need to measure the relative concentration of oxygenated hemoglobin in arterial blood, $SaO_2$, from multiple convenient locations on the body (e.g. the head, torso, or upper limbs), where conventional transmission pulse oximetry cannot be used. Using reflectance oximetry to monitor $SaO_2$ in the fetus during labor, where the only accessible location is the fetal cheek or scalp, provides additional convenient locations for sensor attachment.

While transmission and reflection pulse oximetry are based on similar spectrophotometric principles, it is widely known that reflection pulse oximetry is more challenging to perform and has unique problems. Reflection pulse oximetry can be adversely affected by strong ambient light generated for instance by light sources in the operating room or other light sources used for patient examination or phototherapeutic interventions. Another practical problem in reflection pulse oximetry is the generally very weak pulsatile AC signals that are typically about 10 to 20 times smaller in amplitude compared to AC signals detected by transmission mode pulse oximeter sensors. Consequently, the normalized AC/DC ratios derived from the reflected R or IR photoplethysmograms that are used to compute arterial oxyhemoglobin saturation, $SpO_2$, are very small and range from about 0.001 to 0.005 depending on sensor configuration or placement. In addition, the small amplitudes add considerable noise often leading to unstable readings, false alarms and inaccurate measurements of $SpO_2$.

Improving the quality of the detected photoplethysmographic signals in reflectance pulse oximetry will be beneficial, since inaccuracies caused by noisy and weak pulsatile signals remain one of the major unsolved sources of errors in reflectance pulse oximetry.

SUMMARY OF THE INVENTION

The present invention is directed to holders for a sensor. The holders apply pressure to the sensor to prevent a venous blood signal without dampening the arterial blood signal and are optically opaque to shield ambient light from reaching the sensor.

DETAILED DESCRIPTION OF PREFERRED EMBODIMENTS

Reflectance pulse oximetry sensors can be used to obtain arterial pulse readings from a patient when they are in contact with a surface of the patient's body (e.g., skin on the patient's forehead or another suitable part of the body). Disposable holders are typically used to hold such sensors on the patient's body. When the holders are opaque, they advantageously provide optical shielding and reduce the negative effects of ambient light on the photoplethysmographic signal.

When the pulse oximetry sensor is placed in contact with the patient's skin and pressure is applied to the sensor, the arterial pulse readings are improved considerably. Pressure on a sensor diminishes venous blood in the tissue underneath and, consequently, the disturbing influence of pulsating and non-pulsating venous blood is reduced considerably. The arterial pulse readings are most improved when the amount of pressure is high enough to block venous blood interference, but not so high as to dampen the arterial signal. It is therefore desirable for the holder to press the sensor against the patient's skin with pressure in this range.

Figure 1:
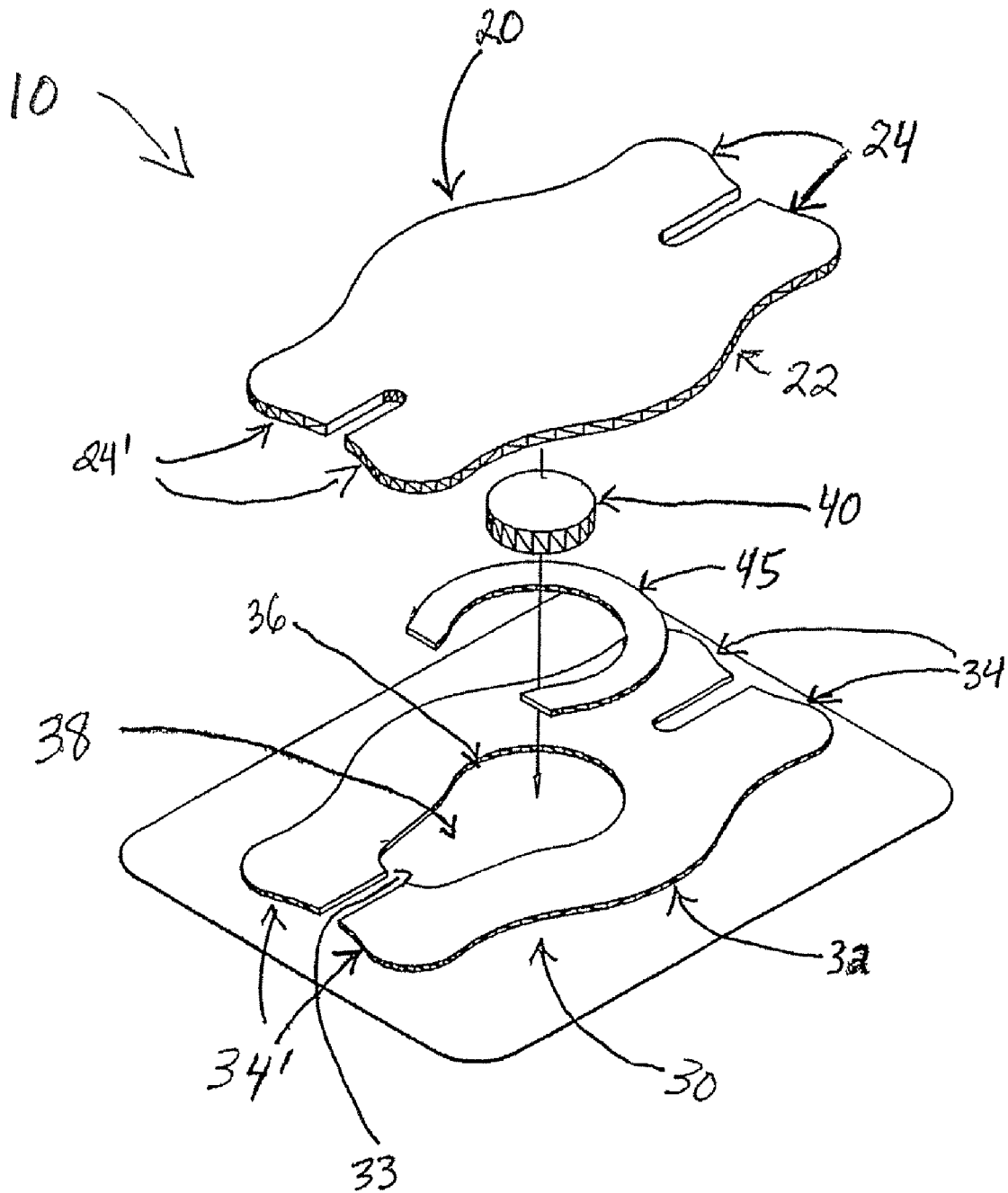
FIG. 1 is an exploded isometric view of a first embodiment of a sensor holder in accordance with the present invention.
Figure 2:
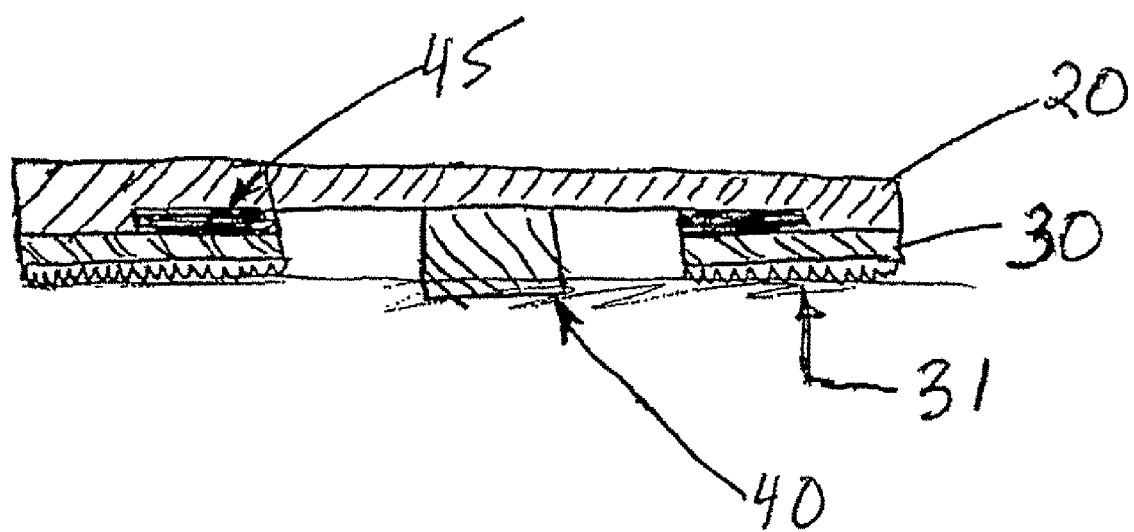
FIG. 2 is a cross-sectional view of the holder of FIG. 1.
Figure 3:
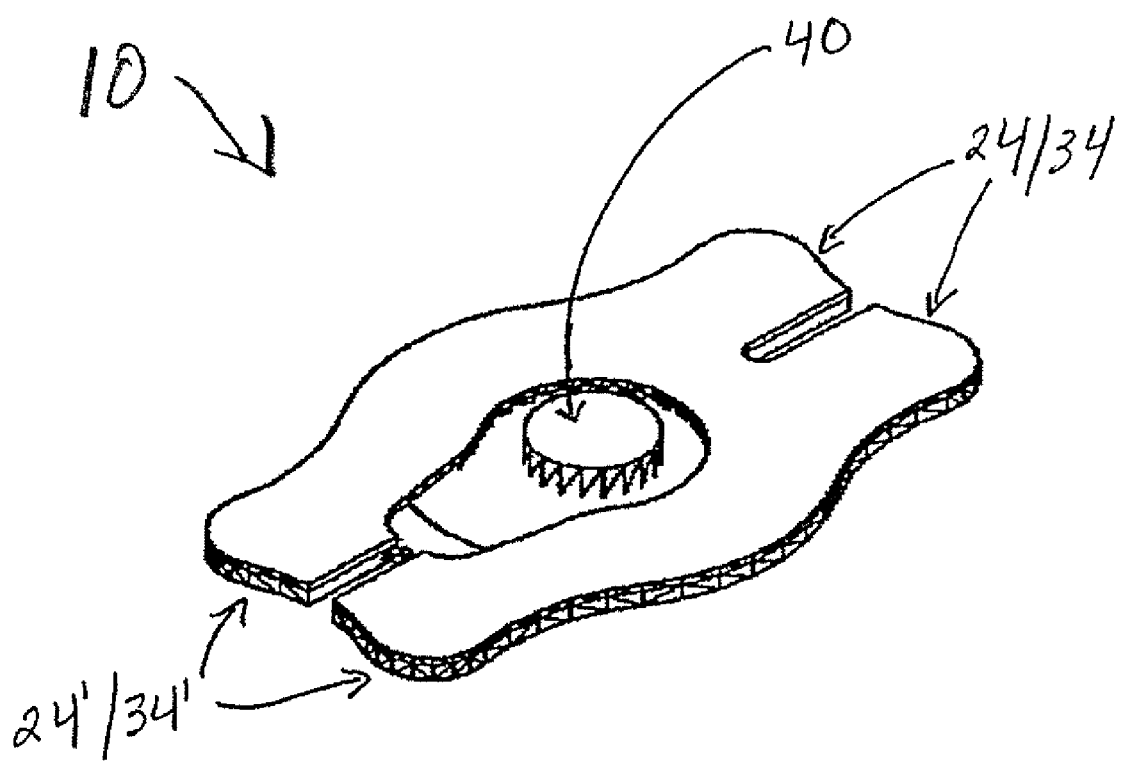
FIG. 3 is a bottom isometric view of the holder of FIG. 1.

With reference to FIGS. 1-3, a first embodiment of the present invention provides a holder 10 for an oximetry sensor (not shown) that simultaneously provides optical shielding, holds the sensor in place, and applies a desired amount of pressure. In the embodiments described herein, the sensor is a reflectance pulse oximetry sensor that is adapted to measure oxygen saturation in living tissue. In alternative embodiments, other types of sensors that benefit from optical shielding and/or a selective degree of pressure may be used instead of the oximetry sensors described herein.

As shown in FIG. 1, the holder 10 of this embodiment is H-shaped and is about 2¾" long and about 1¾" wide. The holder 10 includes a roof portion 20 and a base portion 30.

The roof portion 20 is sufficiently large to accommodate a sensor plus additional regions surrounding the sensor to permit good adhesion and to provide optical shielding. The roof portion 20 is preferably made of material that is optically opaque to provide shielding from ambient light. In addition, the roof portion 20 is preferably flexible so that the holder 10 can curve and conform to differently shaped body surfaces. One example of a suitable material for the roof portion 20 is black, closed cell polyethylene foam having a thickness of 1/16" and a 4 pound density. In the illustrated embodiment, flanges 24, 24" extend out on opposite sides of the central region of the roof portion 20. These flanges are separated so that they can be positioned independent from each other. In the illustrated embodiment, they are spaced apart by about ⅛".

The base portion is shaped to match the roof portion, but with a cutout for aperture 33 for receiving the sensor (not shown). Preferably, this aperture 33 is dimensioned to conform to the shape of the sensor, but is slightly larger than the sensor. For example, if the sensor has a diameter of 0.8", a suitable diameter for the aperture would be about 0.825". The base portion 30 is preferably made of material that is optically opaque and flexible to provide shielding from ambient light and to allow the holder 10 to adhere to curved body surfaces. One example of a suitable material for the base portion 30 is black, closed cell polyethylene foam having a thickness of 1/32" and a 6 pound density. Flanges 34, 34' extend out on opposite sides of the central region and are configured to correspond and adhere to the flanges 24, 24' of the roof portion 20.

To form a useable holder, the roof portion 20 and the base portion 30 are lined up and connected together using, for example, any suitable permanent adhesive such as a contact adhesive system. Once the roof portion 20 and base portion 30 are connected, the lower surface of the roof portion 20 and the inner sidewall 36 of the base portion 30 form an interior cavity 38. The resulting interior cavity 38 will match the contour of the sensor that will be used with the holder 10. This helps to limit motion artifacts that might otherwise interfere with the measurements being made (by providing a tight fit housing around the sensor). The roof portion 20 and the base portion 30 should be aligned during assembly so that the flanges 24, 24' of the roof portion 20 line up with the flanges 34, 34' of the base portion, resulting in a holder with flanges on opposite sides of the central region. These flanges 24/34, 24'/34' help hold the sensor holder 10 to the patient's skin. The holder 10 can be more readily and effectively placed on curved surfaces, such as the forehead of a patient, because each flange 24/34, 24'/34' can be positioned independently to yield greater adhesion, thereby preventing the holder 10 from peeling away from the patient's body during use.

As shown in FIG. 2, the holder 10 includes a layer of adhesive 31 located on the lower surface of the base portion 30 and the flanges 34, 34'. The sensor holder 10 is attached to the skin by this adhesive 31. Preferably, the adhesive 31 is applied to the entire lower surface of the base portion 30 and all the flanges 34, 34', but in alternative embodiments some sections may remain adhesive free. Suitable adhesives include biocompatible skin-friendly medical grade acrylic adhesives such as SPS896, which is an alcohol-soluble acrylic adhesive available from Electromed. Other suitable adhesives include the Adhesives Research 7717 system and the Avery Dennison 416A system. Preferably, the adhesive layer is between about 1¼ and 1¾ mils thick.

A skin friendly, biocompatible Hydrogel adhesive may also be used, particularly on burn patients and babies. Hydrophilic hydrogels are preferred. Hydrogel adhesives allow the holder 10 to be repositioned and yet still provide strong adhesion to the patient's skin. One example of a suitable hydrogel adhesive is Conmed Hydrogel 2000, which is available through the patient care division of Conmed. Other suitable hydrogel adhesives are available from Axelguard and Ludlow, a division of Tyco International. Hydrogel adhesives may be supplied as sheeted gel die cut to meet the required shape.

In operation, a sensor is placed into the interior cavity 38 of the holder 10 and the lower surface of the base portion 30 is adhered to the patient's skin. The sensor is held in place on the patient's skin and the optically opaque material of the holder 10 provides optical shielding from ambient light. The flexibility and elasticity of the holder 10 material allows for easy placement of the holder 10 on curved body surfaces, and also operates to press down on the sensor.

Preferably the holder 10 also includes a pressure application portion 40 that is affixed to the lower surface of the roof portion 20. The pressure application portion 40 may be any type of projection, button, cushion or the like. One example of a suitable material for the pressure application portion 40 is black, closed cell polyethylene foam having a thickness of about ⅛", a diameter of ½" and a 12 pound density. When a sensor is placed in the interior cavity 38 of the holder 10 and the holder 10 is affixed to the patient's body, the sensor presses up on the pressure application portion 40. The roof portion 20 resists this upward force and presses back down on the pressure application portion 40 due to the elasticity of the roof portion 20 and base portion 30. The materials and dimensions described above result in a holder 10 in which the downward force on the sensor will be sufficient to prevent venous blood interference, but not so strong as to interfere with the arterial blood flow or cause the holder to peel away from the skin. Preferably, the bottom of the pressure application portion 40 is not coated with adhesive. In an alternative embodiment (not shown), the pressure application portion 40 may be omitted, and the elasticity of the roof may be relied on to provide the downward force on the sensor.

In the illustrated embodiment, the holder 10 also includes a horseshoe shaped intervening member 45 that adheres to the upper surface of the base portion 30 in the vicinity of the sidewall 36, but does not adhere to the lower surface of the roof portion 20. This intervening member 45 is interposed between the lower surface of the roof portion 20 and the upper surface of the base portion 30 during the manufacture of the holder 10. During manufacture, any suitable adhesive may be placed on the upper surface of the base portion 30 so that the intervening member 45 is adhered to the upper surface of the base portion 30. One example of a suitable material for the intervening member 45 is black, closed cell polyethylene foam having a thickness of 1/32" and a 6 pound density. When a sensor is placed in the holder 10 and the holder 10 is adhered to the patient's skin, the sensor exerts an upward force on the pressure application portion 40, which in turn exerts an upward force on the roof portion 20. Ordinarily, this upward force would act to pull the holder 10 away from the patient's skin by peeling the inner edge upwards. However, since the intervening member 45 is adhered only to the upper surface of the base portion 30, the upward force is directed radially outward, away from the inner sidewall 36 of the base portion 30. As a result, the upward force is applied to the outer edge of the horseshoe-shaped intervening member 45, instead of the inner edge of the inner sidewall 36. This prevents the holder 10 from peeling off.

In an alternative embodiment, the holder 10 also includes a horseshoe shaped intervening member 45 that adheres to the lower surface of the roof portion 20 in the vicinity of the sidewall 36, but does not adhere to the upper surface of the base portion 30. This intervening member 45 is interposed between the lower surface of the roof portion 20 and the upper surface of the base portion 30. During manufacture, any suitable adhesive may be placed on the lower surface of the roof portion 20 so that the intervening member 45 is adhered to the lower surface of the roof portion 20. As stated above, when a sensor is placed in the holder 10 and the holder 10 is adhered to the patient's skin, the sensor exerts an upward force on the pressure application portion 40. The upward force is directed radially outward, away from the inner sidewall 36 of the base portion 30 and applied to the outer edge of the horseshoe shaped intervening member 45 preventing the holder 10 from peeling off the patient's skin.

In another alternative embodiment, the intervening member 45 is omitted and the adhesive between the lower surface of the roof portion 20 and the upper surface of the base portion 30 is omitted in a region surrounding the inner sidewall 36 that roughly corresponds to the shape of the intervening member 45. Again, when a sensor is placed in the holder 10 and the holder 10 is adhered to the patient's skin, the sensor exerts an upward force on the pressure application portion 40. The upward force is directed radially outward, away from the inner sidewall 36 and applied to the outer edge of the horseshoe-shaped region to which no adhesive is applied to prevent peeling.

In a further alternative embodiment useful for neonate patients, the sensor holder 10 includes a roof portion 20 and a base portion 30. However, this embodiment does not include a pressure application portion 40 on the lower surface of the roof portion 20. In addition, this embodiment does not include any flanges 24, 24', 34, 34'. When the roof portion 20 is adhered to the base portion 30, the lower surface of the roof portion 20 and the inner sidewall 36 of the base portion 30 form an interior cavity 38. The interior cavity 38 corresponds to the contours of the sensor.

FIGS. 4-7 show another embodiment of a holder 50 for an oximetry sensor (not shown) that simultaneously provides optical shielding, holds the sensor in place, and applies a desired amount of downward pressure to keep the sensor pressed against the patient's body. The main portion 60, 70 of the holder 50 is preferable integrally molded from an optically opaque material. For example, it may be injection molded from an Evoprene rubber based material (G949) having a 54 Shore A durometer. The main portion in the illustrated embodiment includes a roof portion 60, and a base/wall portion 70 (i.e., a lower portion) that supports the roof 60 above the surface to which the holder 50 is affixed.

The roof 60 and the base/walls 70 are configured so that an interior space is enclosed beneath the roof 60 and between the walls. The footprint of this interior space is preferably dimensioned to be slightly larger than the particular sensor that is being held in place by the holder 50. In the illustrated example, the holder 50 is dimensioned to fit a sensor with a coin-shaped operating end having a diameter of about 0.8" and a thickness of about 0.125", with a flexible cable connected to the side of the coin shaped end. Both the coin-shaped operating end and the distal end of the cable are enclosed within a teardrop shaped housing. The interior space within the holder 50 is similarly teardrop shaped to match this sensor. A suitable diameter for the interior space of the holder for this sensor would be a diameter of 0.825".

The base/wall 70 contains an exit portal 73 through which the sensor's cable can pass. A shroud 74 surrounds and leads up to the portal 73 and is configured to prevent ambient light from entering the interior space beneath the holder 50 when the holder is installed over a sensor.

In the illustrated embodiment, the base/wall 70 is permanently attached to a foundation 80. One suitable way to attach those two components is to insert the foundation 80 into the mold, and injection mold the rubber main portion 60/70 right onto the foundation 80. Black polyethylene film is a suitable material for the foundation 80. In this embodiment, the lower surface of the base/wall 70 is generally horizontal. The foundation 80 may be configured to extend beneath the entire lower horizontal portion of the base/wall 70, but not beneath the interior space of the housing. In other words, the foundation 80 may extend radially inward up to the inner wall 72 of the base/wall 70. In alternative embodiments, instead of extending radially inward all the way to the inner wall 72, the foundation 80 may end before reaching that point. In the illustrated embodiment, the foundation 80 includes four tabs 85 that extend about ½" out past the base/wall 70 on opposite sides of the holder 50. In still other alternative embodiments, the foundation may be omitted completely, and the base/wall 70 is applied directly to the patient.

An adhesive is applied to the bottom 82 of the foundation 80, including the bottom of the tabs 85. In addition, any portion of the base/wall 70 that will be in contact with the patient's body during use should preferably also be coated with the adhesive. (In embodiments that do not have a foundation 80, the adhesive is applied to the bottom of the base/wall 70.) Note that any of the adhesives described above in connection with the FIG. 1 embodiment may be used for this embodiment as well.

When used for the 0.8" diameter sensor described above, a suitable diameter for the interior space for the holder 50 is about 0.825", and a suitable exterior diameter of the base/wall 70 is about 1.6" in diameter. A suitable length for the foundation 80 (including the tabs 85) is about 3".

Figure 5:
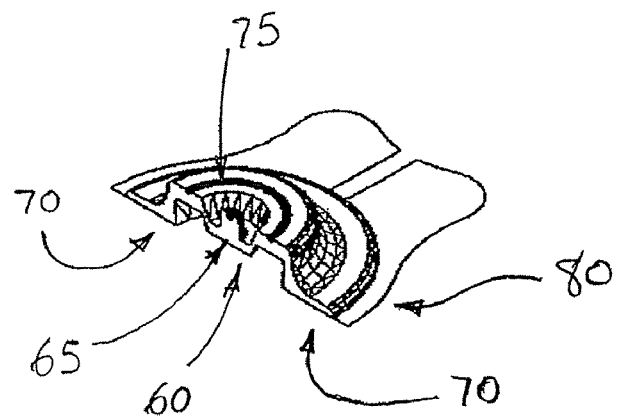
FIG. 5 is a top isometric cross-sectional view of the holder of FIG. 4.
Figure 6:
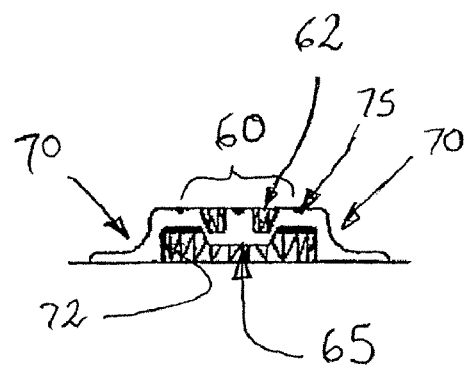
FIG. 6 is a cross-sectional view of the holder of FIG. 4.
Figure 7:
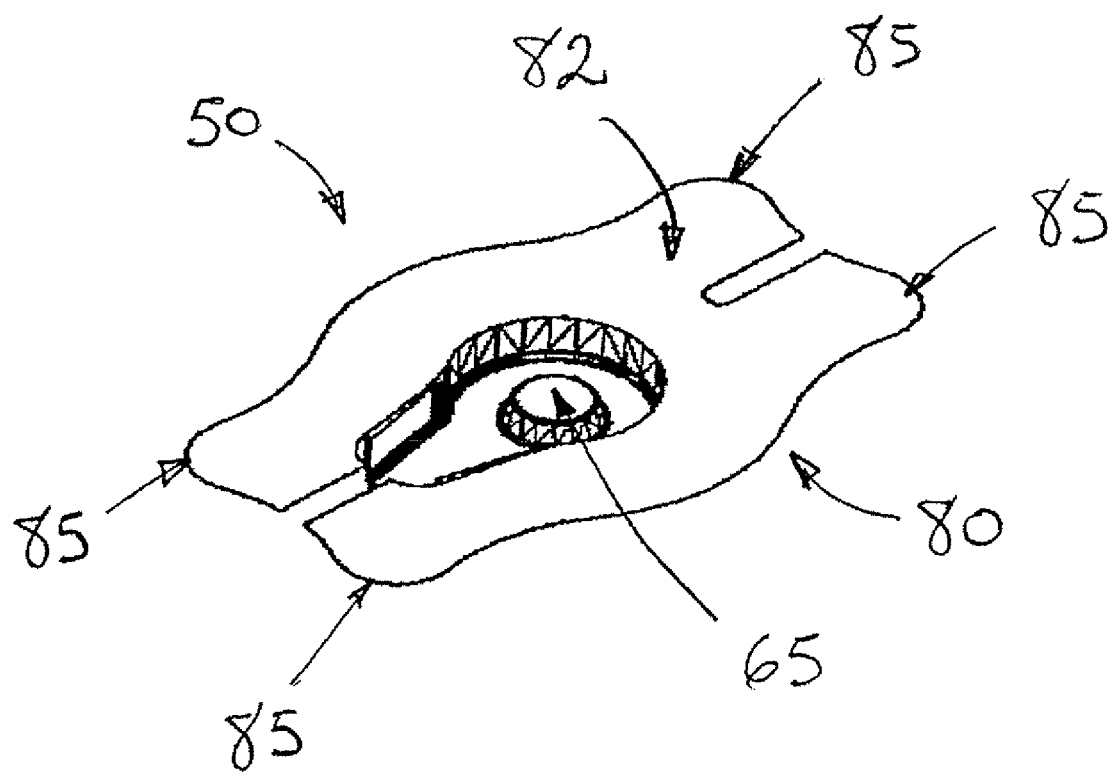
FIG. 7 is a bottom isometric view of the holder of FIG. 4

As best seen in FIGS. 5-7, the roof 60 includes a protrusion or button 65 that extends down into the interior space that is confined beneath the holder 50. One suitable diameter for the button 65 is 0.33." In order to impart the desired downward force on the sensor, the button 65 must be dimensioned so that when a sensor is positioned beneath the holder 50, and the holder 50 is stuck on the surface of the patient's body with an adhesive as described above, the lower surface of the button 65 presses down on the top surface of the sensor. In order for this to occur, the resting height of the lower surface of the button 65 with respect to the surface to which it is affixed must be less than the height of the sensor above that surface. For example, if the sensor is 0.125" high, the button 65 may be dimensioned so that the lower surface of the button 65 is ordinarily held by the roof 60 and base/wall 70 at a height of about 0.8" above the surface to which the holder 50 is affixed. When the holder 50 is so dimensioned, installation of the holder 50 on top of the sensor will cause the bottom of the button 65 to press down on the sensor.

The base/wall 70 and the roof 60 are configured so that the button 65 can float up and down like a spring. As a result, when the holder 50 is installed on top of a sensor and affixed to the surface of the patient's body, the sensor (which is taller than the resting height of the button 65) will press up against the button 65. In response, the spring effect will push the button 65 down against the sensor, thereby exerting a downward force on the sensor.

The amount of downward force that is applied to the sensor will depend on the structure on the base/wall 70 and the roof 60, the dimension of those structures, and the materials used to form those structures. For example, increasing the diameter of the button 65 will increase the downward force that is applied to the sensor, and decreasing the diameter of the button will result in a corresponding decrease in that force. In addition, decreasing the resting height of the lower surface of the button 65 above the surface to which it is adhered will result in a higher downward force being applied to the sensor. Using a thicker material to form the roof 60 and the base/wall 70 will also increase the force that is applied to the sensor.

Preferably, an annular trough 75 is cut into the top roof 60, positioned radially beyond the button 65. The downward force exerted by button 65 on the sensor can also be adjusted by changing the dimensions of this trough 75. (Making the trough 75 deeper will result in less downward force being applied to the sensor.) Optionally, a second annular trough 62 may be cut into the top surface of the roof portion 60 above the button 65. Making this second trough 62 deeper and wider will also result in less downward force being applied to the sensor. This second trough 62 may also be omitted altogether (as it is in the FIG. 8 embodiment). In this case, the downward force applied to the sensor will be larger.

Figure 8:
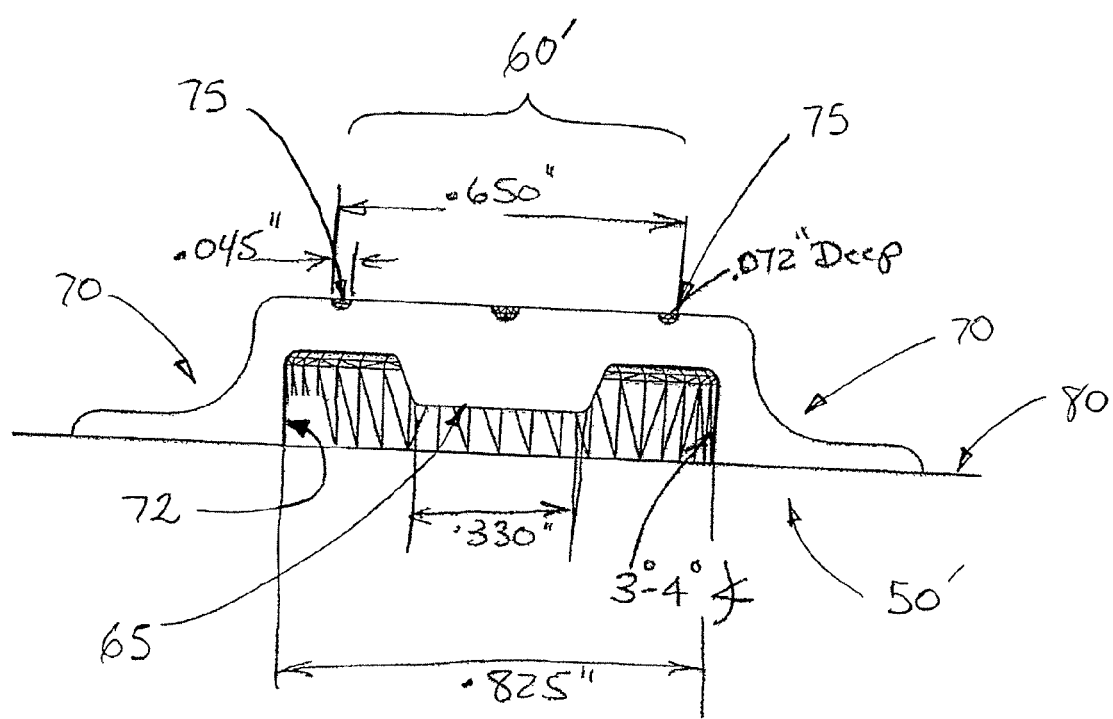
FIG. 8 is a cross-sectional view of a third embodiment of a sensor holder in accordance with the present invention.

FIG. 8 depicts another embodiment of a holder 50'. The holder 50' of this embodiment is very similar to the holder 50 described above in connection with FIGS. 4-7, and corresponding reference numbers refer to similar structure. In most cases, the above description of the FIG. 4 embodiment applies to the holder 50'. However, the roof 60' of the holder 50' does not have the second (interior) annular trough above the button 65. In addition, the interior walls 72 surrounding the interior space are not exactly vertically. Instead, those walls 72 are undercut, with the walls angled slightly outward (i.e., so that their inner diameter increases slightly with height). A preferred angle of inclination for the interior walls 72 is between about 3° and about 4°. Angling the wall 72 in this manner makes the base/wall 70 thinner near the top of the base/wall 70, close to where the roof 60' joins the base/wall 70. This thinning of the side walls provides extra flexibility and increases the spring effect in the holder 50', making it easier for the button 65 to float up and down like a spring.

When the holder 50' is placed on top of a sensor (not shown), the sensor pushes up against the button 65, which pushes up against the entire roof portion 60'. The upward force applied to the roof is transmitted through the base/wall 70 during use to the bottom of the holder 50', which is glued to the surface of the body as described above. This upward force acts in a direction that tends to pull the holder 50' away from the surface to which it is adhered. If the walls were not undercut, this force would be directly normal to the surface to which the holder is adhered at the bottom corner of the interior wall 72, and the adhesive might start peeling away from the body at the inside edge of the glued portion. However undercutting the interior sidewall at an angle of between about 3°-4° as shown causes the upward load to be distributed away from the edge of the adhesive contact region and more towards the center of the adhesive region. As a result, the holder is less likely to start peeling off from the surface to which it is adhered. This arrangement permits the desired downward force on the sensor to maintained over long periods of time by reducing the chance that the holder will peel away at the inside edge from the surface to which it is applied (which would result in a decreased downward force at the sensor).

Figure 4:
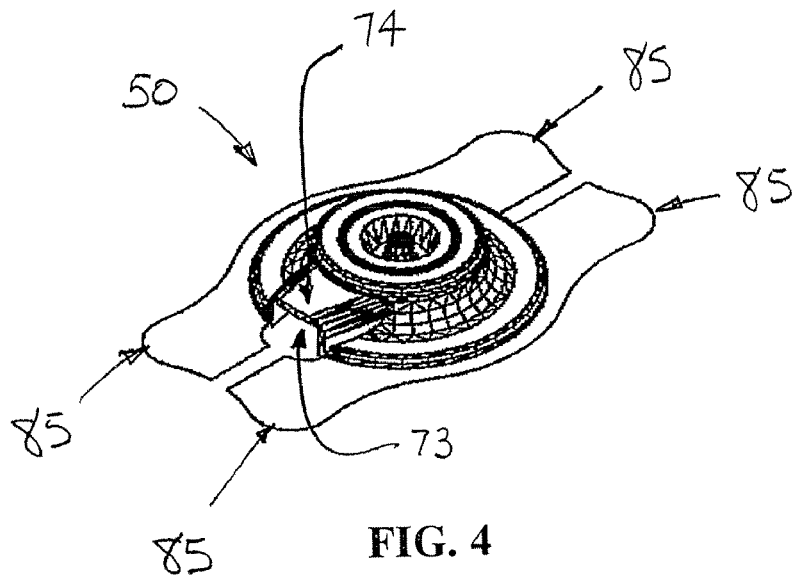
FIG. 4 is a top isometric view of a second embodiment of a sensor holder in accordance with the present invention.

Optionally, the undercutting described above in connection with the FIG. 8 embodiment may also be used in the FIG. 4 embodiment.

Figure 9:
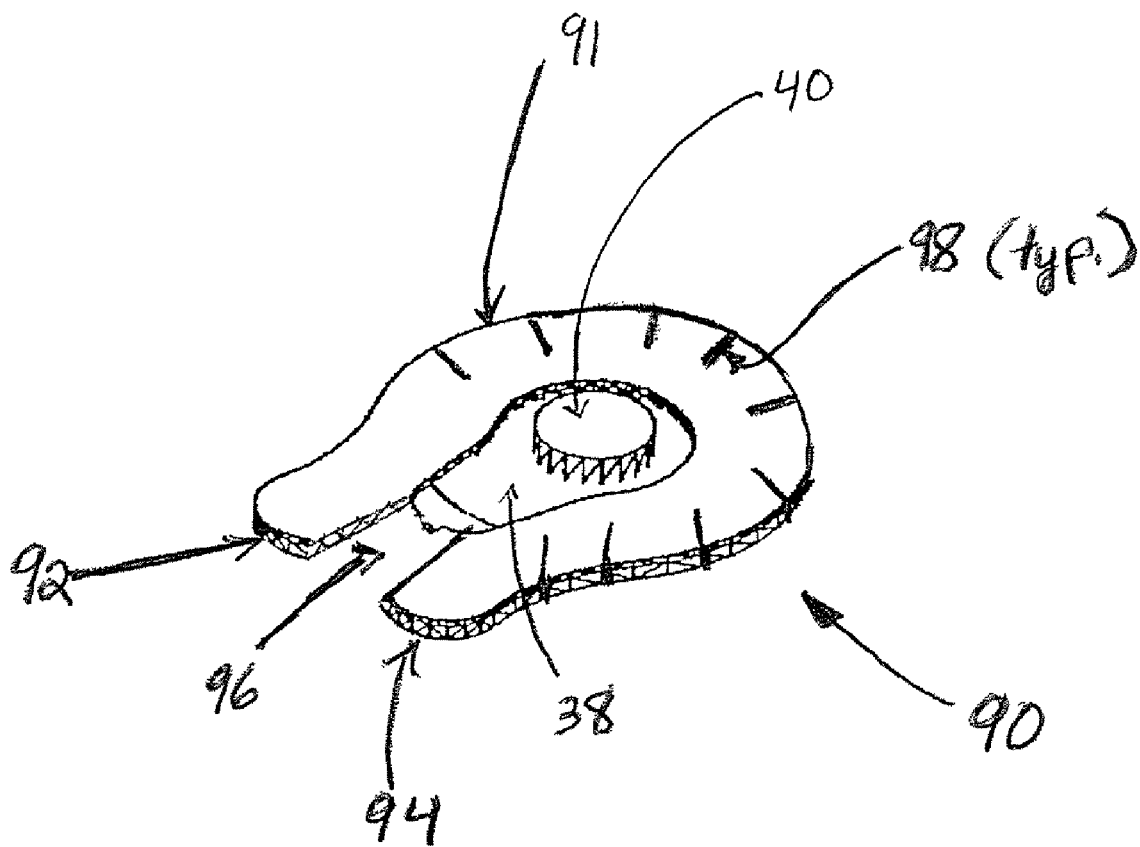
FIG. 9 is a bottom isometric view of a fourth embodiment of a sensor holder in accordance with the present invention.

FIG. 9 shows another embodiment of a holder 90 for an oximetry sensor (not shown) that simultaneously provides optical shielding, holds the sensor in place, and applies a desired amount of downward pressure to keep the sensor pressed against the patient's body. The holder 90 of this embodiment is similar to the holder 10 described above in connection with FIGS. 1-3, and corresponding reference numbers refer to similar structure. In most cases, the above description of the holder 10 in FIGS. 1-3 applies to the holder 90. However, in the holder 90, a first flange 92 and a second flange 94 extend out on the same side of the central region of the base portion 30, and there are no flanges on the opposite side. Preferably, the flanges 92, 94 extend out from the central body on the same side as the exit portal 96, through which the sensor's cable can pass. The distance between the flanges 92, 94 is preferably greater than the distance between the flanges in the FIG. 3 embodiment, to permit the tail end of the sensor to lift up away from the surface of the skin without lifting the sensor holder. For example, the flanges 92, 94 may be spaced apart by about ¼". Optionally, a plurality of radial slits 98 may be cut into the holder 90, preferably on the portions of the holder 90 that do not have the flanges 92, 94. The radial slits 98 are cut from the outer edge 91 of the holder 90 inward toward the center of the holder, but preferably do not extend so far inward so as to reach the interior cavity 38. In the illustrated embodiment, the radial slits 98 are cut all the way through the sensor holder 90. In alternative embodiments (not shown), the radial slits do not go all the way through the holder. For example, the slits may cut at least halfway into the holder from the top of the holder or from the bottom of the holder or about ¼ of the way in from each of the top and bottom of the holder at the same location. These slits serve to break up the mechanical strength of the foam material. A suitable spacing for the slits 98 is about 0.2" apart. The radial slits 98 provide additional flexibility to the holder 90, allowing the holder 90 to stick better on curved surfaces.

Optionally, the radial slits described above in connection with the FIG. 9 embodiment may also be used in any of the other embodiments described above.

Additional advantages and modifications will readily occur to those skilled in the art. For example, the features of any of the embodiments may be used singularly or in combination with any other of the embodiments of the present invention. Accordingly, various modifications may be made without departing from the spirit or scope of the general inventive concept.

We claim:

1. A sensor holder for holding a reflectance type oximetry sensor against a patient's skin, the sensor holder comprising:
a base portion having an adhesive bottom surface adapted to temporarily stick the base portion onto the patient's skin, the base portion having a central void therein that is bordered by at least one inner wall; and
a roof portion positioned above the central void and attached to the base portion so as to form an interior cavity between the roof portion and the at least one inner wall, wherein the interior cavity is dimensioned to accept the oximetry sensor,
wherein the roof portion and the base portion are configured so that when the sensor holder is positioned over the oximetry sensor and stuck on a patient's skin, the oximetry sensor exerts an upward force against the roof portion, and an interaction between the roof portion and the base portion causes the roof portion to exert a downward force on the oximetry sensor,
wherein the roof portion and the base portion are configured so that the upward force against the roof portion is directed radially outward, with respect to the central void, from the at least one inner wall,
wherein the roof portion and the base portion are connected radially beyond a region that is adjacent to the at least one inner sidewall and extends radially outward from the at least one inner sidewall, and
wherein the roof portion and the base portion are not connected within the region.

2. The sensor holder of claim 1, wherein the downward force exerted on the oximetry sensor is high enough to block venous blood flow in a region of skin beneath oximetry, the sensor, but not high enough to block arterial blood flow in the region.

3. The sensor holder of claim 1, wherein the roof portion is optically opaque, and wherein the apparatus further comprises a shroud for blocking light that is positioned about an entrance to the interior cavity.

4. The sensor holder of claim 1, wherein the base portion and the roof portion are made of substantially flat flexible material, the region is horseshoe shaped, and the base portion and the roof portion are connected using a permanent adhesive that is applied radially beyond the horseshoe shaped region, but is not applied within the horseshoe shaped region.

5. The sensor holder of claim 4, wherein the sensor holder has at least one radial slit running inwards from an outer edge of the sensor holder.

6. The sensor holder of claim 4, further comprising at least two flanges that extend radially outward from the base portion, the flanges having a lower surface with an adhesive disposed thereon, and wherein the roof portion is optically opaque.

7. The sensor holder of claim 1, wherein the base portion and the roof portion are made of substantially flat flexible material and the region is horseshoe shaped, and wherein the sensor holder further comprises a substantially flat horseshoe shaped intervening member that is affixed to either the lower surface of the roof portion or an upper surface of the base portion in the horseshoe shaped region.

8. The sensor holder of claim 7, wherein the sensor holder has at least one radial slit running inwards from an outer edge of the sensor holder.

9. The sensor holder of claim 7, further comprising at least two flanges that extend radially outward from the base portion, the flanges having a lower surface with an adhesive disposed thereon, and wherein the roof portion is optically opaque.

10. The sensor holder of claim 9, further comprising a protrusion configured to extend down from the roof portion into the interior cavity, and wherein the roof portion is black, closed cell polyethylene foam having a thickness of about $1/16$th of an inch, the base portion is black, closed cell polyethylene foam having a thickness of about $1/32$nd of an inch, and the protrusion has a thickness of about $1/8$th inch.

* * * * *